US010674939B1

(12) United States Patent
Jones et al.

(10) Patent No.: US 10,674,939 B1
(45) Date of Patent: *Jun. 9, 2020

(54) MEASURING USER RESPIRATION AT EXTREMITIES

(71) Applicant: Vardas Solutions LLC, El Dorado Hills, CA (US)

(72) Inventors: Alex Jones, Carlsbad, CA (US); Chad Vardas, El Dorado Hills, CA (US); Alejandro Jimenez, Maple Grove, MN (US); Jan Niewiadomski, Aquebogue, NY (US)

(73) Assignee: VARDAS SOLUTIONS LLC, El Dorado Hills, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/284,955

(22) Filed: Feb. 25, 2019

Related U.S. Application Data

(63) Continuation of application No. 16/275,153, filed on Feb. 13, 2019.

(51) Int. Cl.
  *A61B 5/08* (2006.01)
  *A61B 5/00* (2006.01)
  *A61B 5/053* (2006.01)

(52) U.S. Cl.
  CPC .......... *A61B 5/0816* (2013.01); *A61B 5/0531* (2013.01); *A61B 5/681* (2013.01); *A61B 5/7225* (2013.01); *A61B 5/7278* (2013.01)

(58) Field of Classification Search
  None
  See application file for complete search history.

(56) References Cited

U.S. PATENT DOCUMENTS

| 5,682,898 A | 11/1997 | Aung et al. |
| 5,722,997 A | 3/1998 | Nedungadi et al. |
| 6,212,427 B1 | 4/2001 | Hoover et al. |
| 6,305,943 B1 | 10/2001 | Pougatchev et al. |

(Continued)

FOREIGN PATENT DOCUMENTS

| CN | 103211603 A | 7/2013 |
| CN | 103690166 A | 4/2014 |

(Continued)

OTHER PUBLICATIONS

Jia et al., "Monitoring a Person's Heart Rate and Respiratory Rate on a Shared Bed Using Geophones," In. Proceedings of the 15th ACM Conference on Embedded Network Sensor Systems, Nov. 6, 2017, Retrieved from http://www.winlab.rutgers.edu/-sugangli/papers/Sensys_2017.pdf, 16 pages.

(Continued)

*Primary Examiner* — Etsub D Berhanu
(74) *Attorney, Agent, or Firm* — Dergosits & Noah LLP

(57) ABSTRACT

Systems and methods measure impedance across a user's chest during respiration to determine a rate of respiration. With AC-modulation contacts separated from impedance-measuring contacts, analog filtering to remove EMI, a bridging capacitor to remove DC noise, and digital filtering to further remove EMI, a user's respiration may be measured with the AC-modulation contacts and the impedance-measuring contacts placed at user extremities.

18 Claims, 10 Drawing Sheets

(56) References Cited

U.S. PATENT DOCUMENTS

| | | | |
|---|---|---|---|
| 6,358,201 B1 | 3/2002 | Childre et al. | |
| 6,377,845 B1 | 4/2002 | Kinast | |
| 6,656,116 B2 | 12/2003 | Kim et al. | |
| 6,836,681 B2 | 12/2004 | Stabler et al. | |
| 7,117,032 B2 | 10/2006 | Childre et al. | |
| 7,163,512 B1 | 1/2007 | Childre et al. | |
| D554,266 S | 10/2007 | Striepe et al. | |
| 7,462,151 B2 | 12/2008 | Childre et al. | |
| 7,618,378 B2 | 11/2009 | Bingham et al. | |
| 7,691,049 B2 | 4/2010 | Wood et al. | |
| 8,002,711 B2 | 8/2011 | Wood et al. | |
| 8,066,637 B2 | 11/2011 | Childre et al. | |
| 8,123,696 B2 | 2/2012 | Childre et al. | |
| 8,301,232 B2 | 10/2012 | Albert et al. | |
| 8,306,621 B2 | 11/2012 | Kim et al. | |
| 8,509,882 B2 | 8/2013 | Albert et al. | |
| 8,523,758 B1 | 9/2013 | Kirby et al. | |
| 8,543,197 B2 | 9/2013 | Striepe et al. | |
| 8,700,137 B2 | 4/2014 | Albert | |
| 8,764,673 B2 | 7/2014 | McCraty et al. | |
| 8,936,556 B2 | 1/2015 | Lee et al. | |
| 8,938,288 B2 | 1/2015 | Wood et al. | |
| 9,026,202 B2 | 5/2015 | Albert | |
| 9,113,612 B2 | 8/2015 | Koyrakh et al. | |
| 9,113,807 B2 | 8/2015 | Koyrakh et al. | |
| 9,220,430 B2 | 12/2015 | Albert | |
| 9,247,911 B2 | 2/2016 | Galloway et al. | |
| 9,254,092 B2 | 2/2016 | Albert et al. | |
| 9,254,095 B2 | 2/2016 | Galloway et al. | |
| 9,351,654 B2 | 5/2016 | Albert | |
| 9,420,956 B2 | 8/2016 | Gopalakrishnan et al. | |
| 9,572,499 B2 | 2/2017 | Gopalakrishnan et al. | |
| 9,579,062 B2 | 2/2017 | Albert | |
| 9,610,017 B2 | 4/2017 | Casal et al. | |
| 9,699,528 B2 | 7/2017 | Dixit et al. | |
| 9,830,832 B2 | 11/2017 | Warren et al. | |
| 9,913,612 B2 | 3/2018 | Banet | |
| 10,117,598 B1* | 11/2018 | Mouradian | A61B 5/0816 |
| 2005/0033189 A1 | 2/2005 | McCraty et al. | |
| 2005/0124906 A1 | 6/2005 | Childre et al. | |
| 2005/0209504 A1 | 9/2005 | Elliott et al. | |
| 2005/0288601 A1 | 12/2005 | Wood et al. | |
| 2007/0021675 A1 | 1/2007 | Childre et al. | |
| 2007/0270668 A1 | 11/2007 | Childre et al. | |
| 2007/0299354 A1 | 12/2007 | Striepe et al. | |
| 2008/0035147 A1 | 2/2008 | Kirby et al. | |
| 2008/0319513 A1 | 12/2008 | Pu et al. | |
| 2009/0137915 A1 | 5/2009 | Childre et al. | |
| 2009/0281400 A1 | 11/2009 | McCraty et al. | |
| 2010/0041967 A1 | 2/2010 | McCraty et al. | |
| 2010/0174205 A1 | 7/2010 | Wegerif | |
| 2011/0004047 A1 | 1/2011 | Braspenning et al. | |
| 2011/0301435 A1 | 2/2011 | Albert et al. | |
| 2011/0301439 A1 | 12/2011 | Albert et al. | |
| 2012/0172689 A1 | 7/2012 | Albert et al. | |
| 2013/0197320 A1 | 8/2013 | Albert et al. | |
| 2014/0050321 A1 | 2/2014 | Albert et al. | |
| 2014/0066798 A1 | 3/2014 | Albert | |
| 2014/0128758 A1 | 5/2014 | Galloway et al. | |
| 2014/0187974 A1 | 7/2014 | Banet et al. | |
| 2014/0194760 A1 | 7/2014 | Albert | |
| 2014/0221859 A1 | 8/2014 | Albert | |
| 2014/0228665 A1 | 8/2014 | Albert | |
| 2014/0276162 A1 | 9/2014 | Albert et al. | |
| 2015/0018660 A1 | 1/2015 | Thomson et al. | |
| 2015/0018702 A1 | 1/2015 | Galloway et al. | |
| 2015/0045641 A1 | 2/2015 | Rule | |
| 2015/0073285 A1 | 3/2015 | Albert et al. | |
| 2015/0087952 A1 | 3/2015 | Albert et al. | |
| 2015/0126847 A1 | 5/2015 | Balji et al. | |
| 2015/0164349 A1 | 6/2015 | Gopalakrishnan et al. | |
| 2015/0238147 A1 | 8/2015 | Figgatt et al. | |
| 2015/0265164 A1 | 9/2015 | Gopalakrishnan et al. | |
| 2015/0297134 A1 | 10/2015 | Albert et al. | |
| 2015/0317885 A1 | 11/2015 | Ramstein et al. | |
| 2015/0320328 A1 | 11/2015 | Albert | |
| 2016/0074674 A1 | 3/2016 | Kohli et al. | |
| 2016/0184518 A1 | 6/2016 | Freeman et al. | |
| 2016/0234572 A1 | 8/2016 | Dixit | |
| 2016/0235319 A1 | 8/2016 | Albert | |
| 2016/0242665 A1 | 8/2016 | Galloway et al. | |
| 2016/0242697 A1 | 8/2016 | Albert | |
| 2016/0249823 A1 | 9/2016 | Galloway et al. | |
| 2016/0331247 A1 | 11/2016 | Albert | |
| 2017/0224273 A1 | 8/2017 | Vardas | |
| 2017/0273574 A1* | 9/2017 | Wu | A61B 5/14542 |
| 2017/0325700 A1 | 11/2017 | Lane et al. | |
| 2018/0312167 A1 | 11/2018 | Kundu | |

FOREIGN PATENT DOCUMENTS

| | | |
|---|---|---|
| KR | 20150099430 A | 8/2015 |
| WO | 0028892 A1 | 5/2000 |
| WO | 2000051677 A2 | 9/2000 |
| WO | 2005015157 A2 | 2/2005 |
| WO | 2005044092 A2 | 5/2005 |
| WO | 2010014170 A1 | 2/2010 |
| WO | 2011156374 A2 | 12/2011 |
| WO | 2012158190 A1 | 11/2012 |
| WO | 2013112979 A1 | 8/2013 |
| WO | 2014028899 A1 | 2/2014 |
| WO | 2014036436 A1 | 3/2014 |
| WO | 2014074913 A1 | 5/2014 |
| WO | 2014107700 A1 | 7/2014 |
| WO | 2014145927 A1 | 9/2014 |
| WO | 2014172451 A1 | 10/2014 |
| WO | 2015035251 A1 | 3/2015 |
| WO | 2015089484 A1 | 6/2015 |
| WO | 2015164404 A1 | 10/2015 |
| WO | 2015171764 A1 | 11/2015 |
| WO | 2016183515 A1 | 11/2016 |

OTHER PUBLICATIONS

Notification of Transmittal of the International Search Report and the Written Opinion of the International Searching Authority, International Application No. PCT/US2018/037156, dated Sep. 21, 2018, 22 pages.

Pan et al., "A Real-Time QRS Detection Algorithm," IEEE Transactions on Biomedical Engineering, vol. BME-32, No. 3, Mar. 1985, pp. 230-236.

ADS1291, ADS1292, ADS1292R, Texas Instruments, SBAS502B, Dec. 2011—Revised Sep. 2012, p. 12 and pp. 56-60.

Amit K. Gupta, "Respiration Rate Measurement Based on Impedence Pneumography," Texas Instruments, Application Report, SBAA181—Feb. 2011, 11 pages.

Peace of mind in your pocket, Jun. 11, 2018, https://www.alivecor.com, Retrieved Jul. 31, 2018, pp. 1-5.

Compare Apple Watch Models, Jun. 6, 2018, https://www.apple.com/watch/compare/, Retrieved Jun. 29, 2018, pp. 1-4.

Apple Watch Series 3, Jun. 6, 2018, www.apple.com/watch, Retrieved Jun. 29, 2018, pp. 1-6.

Compare Apple Watch Models, Jun. 7, 2018, https://www.apple.com/watch/compare/, Retrieved Jun. 29, 2018, pp. 1-3.

Linea No. 10, Apr. 15, 2018, https://www.caeden.com, Retrieved Jul. 31, 2018, pp. 1-2.

The Caeden Sona Connected Bracelet for Mind and Body, Jan. 12, 2018, https://www.caeden.com:80/sona/, Retrieved Jul. 31, 2018, pp. 1-6.

Fitbit alta HR, Move to the beat of you, Jun. 9, 2018, https://www.fitbit.com/altahr, Retrieved Jul. 26, 2018, pp. 1-7.

Fitbit motivates you to reach your health and fitness goals by tracking your activity, exercise, sleep, weight and more, Jun. 11, 2018, https://www.fitbit.com/home, Retrieved Jul. 26, 2018, pp. 1-3.

Track, analyze and share your data, Jun. 8, 2018, https://buy.garmin.com/en-US/US/wearabletech/wearables/c10001-c10002-p1.html, Retrieved Jul. 31, 2018, pp. 1-3.

(56) References Cited

OTHER PUBLICATIONS

Take Charge of How You Feel, Release Stress/Find Balance/Build Resilience, Jun. 7, 2018, https://store.heartmath.com/, Retrieved Jul. 26, 2018, pp. 1-5.
The Journey of Happiness, Dec. 3, 2017, http://www.iheha.com:8/hk-en/index.php, Retrieved Jul. 31, 2018, pp. 1-3.
Wearable relief, rack your stress, train for relief, Jun. 11, 2018, https://getlief.com, Retrieved Jul. 26, 2018, pp. 1-4.
When you're calm you'll hear peaceful weather sounds, Jun. 5, 2018, https://www.choosemuse.com, Retrieved Jul. 26, 2018, pp. 1-5.
Lead a healthier, happier life by managing your stress, Feb. 19, 2018, https://thepip.com/en-us, Retrieved Jul. 31, 2018, pp. 1-6.
Breathe better, Sit better, Feel better, with Prana, May 18, 2018, http://prana.co/, Retrieved Jul. 31, 2018, pp. 1-12.
Make Your Clothes Smart, Jun. 7, 2018, https://www.spire.io/, Retrieved Jul. 26, 2018, pp. 1-3.
Thync's bioelectronics wearable shows promise in psoriasis pilot, Oct. 9, 2017, http://fiercebiotech.com:8/medtech/thync-s-bioelectronics-wearable-shows-promise-psoriasis-pilot, Retrieved Jul. 31, 2018, pp. 1-3.
Breakthrough Bioelectronic Therapies, Jun. 10, 2018, https://www.thync.com/, Retrieved Jul. 31, 2018, pp. 1-3.
Want to Win a Free Set of Touchpoints?, Feb. 24, 2018, https://www.thetouchpointsolution.com, Retrieved Jul. 26, 2018, pp. 1-5.
The world's first stress balancing bracelet, Oct. 4, 2017, http://thewellbe.com/, Retrieved Jul. 31, 2018, pp. 1-8.
International Search Report and Written Opinion, PCT/US17/17065, dated May 16, 2017, 22 pages.
Google translation of CN103211603, Jul. 24, 2013, Mental stress detecting, tracking and feedback system, chrome-extension://nlipoenfbbikpbjkfpfillcgkoblgpmj/edit.html, retrieved Jan. 30, 2019, 4 pages.
Kohli et al., Prototype development of an electrical impedance based simultaneous resopiratory and cardiac monitoring system for gated radiotherapy, BioMedical Engineering Online (2014) 13:144, http://www.biomedical-engineering-online.com/content/13/1/144.
Trobec et al., Two Proximal Skin Electrodes—A Respiration Rate Body Sensor, Sensors (2012) 12, pp. 13813-13828; www.mdpi.com/journal/sensors.
Google translation for CN103690166 A, https://patents.google.com/patent/CN103690166B/en, retrieved Feb. 27, 2019, 6 pages.
Notification of Transmittal of International Search Report and the Written Opinion of th International Searching Authority, or the Declaration, International Application No. PCT/US19/18624, dated May 10, 2019, 7 pages.

\* cited by examiner

MEASURING USER RESPIRATION AT EXTREMITIES

CROSS-REFERENCE TO RELATED CASES

The present application claims priority to U.S. patent application Ser. No. 16/275,153, entitled "MEASURING USER RESPIRATION AT EXTREMITIES," filed on Feb. 13, 2019, which is hereby incorporated by reference. The present application is related to International Application No. PCT/US18/37156, entitled "METHODS AND SYSTEMS FOR PROVIDING A BREATHING RATE CALIBRATED TO A RESONANCE BREATHING FREQUENCY," filed on Jun. 12, 2018, and to U.S. patent application Ser. No. 16/006,558, entitled "METHODS AND SYSTEMS FOR PROVIDING A BREATHING RATE CALIBRATED TO A RESONANCE BREATHING FREQUENCY," filed on Jun. 12, 2018 which is a continuation-in-part of U.S. patent application Ser. No. 15/428,115, entitled "STRESS MANAGEMENT USING BIOFEEDBACK," filed on Feb. 8, 2017, which claims priority to U.S. Provisional Patent Application No. 62/292,450, entitled "WEARABLE APPARATUS WITH BIOFEEDBACK," filed on Feb. 8, 2016, each of which is hereby incorporated by reference.

TECHNICAL FIELD

The present disclosure relates to the field of sensors, including, more particularly, to methods and systems for measuring a user's respiration.

BACKGROUND

It is desirable to be able to measure the respiration rate of a user. For example, heart rate generally increases upon inhalation and decreases upon exhalation, i.e., some heart rate variation is induced by respiration. Heart Rate Variability (HRV) is the variation of the time intervals between heart beats. An increase in HRV is desirable because it is indicative of a heart rate that is variable and responsive to physiological demands. HRV is greatest when individuals breathe at a frequency that is particular to that individual—their resonance breathing frequency (or "resonance breathing rate"). Respiratory Sinus Arrhythmia (RSA) occurs when Heart Rate Variability (HRV) is in synchrony with respiration, shown when variability on an ECG is shortened during inspiration ("inhalation") and prolonged during expiration ("exhalation"). Thus, it may be desirable to determine a user's respiration rate and whether that rate is in synchrony with HRV.

Some existing systems and methods for measuring a user's respiration rate rely on a change in the impedance of the user's chest. That change in impedance is caused by two aspects of a user's respiration: a change in the volume of gas in relation to the surrounding tissue; and a change in the electrical path length across the chest that is caused by the expansion of the chest. The impedance increases as the gas volume and path length increase. To measure that change, electrodes may be placed on the user on either side of the chest and modulation signals (excitation signals of an alternating current signal at a known frequency) may be passed between the electrodes. A base voltage signal is created between the electrodes by the impedance of the user's chest to the AC current when the user has completely exhaled. A respiration voltage signal is imposed on the base voltage signal by the increase in impedance caused by the user's respiration. To determine the respiration voltage signal, the resulting combined voltage signal is demodulated. The respiration frequency is determined from the resulting demodulated voltage signal.

FIG. 1 is a prior art circuit diagram for a Texas Instruments ADS1292R from the data sheet for the Texas Instruments ADS1292R, which is a low-power, 2-channel, 24-bit analog-to-digital converter. The datasheet for a Texas Instruments ADS1292R discloses that a feature of the ADS1292R is an integrated respiration impedance measurement. FIG. 1 depicts FIG. 56 from the data sheet for the TI ADS1292R. The pin assignments from the ADS1292R are provided in TABLE 1.

TABLE 1

NAME; TERMINAL; FUNCTION; DESCRIPTION

AVDD; 12; Supply; Analog supply
AVSS; 13; Supply; Analog ground
CLK; 17; Digital input; Master clock input
CLKSEL; 14; Digital input; Master clock select
CS; 18; Digital input; Chip select
DGND; 24; Supply; Digital ground
DIN; 19; Digital input; SPI data in
DOUT; 21; Digital output; SPI data out
DRDY; 22; Digital output; Data ready; active low
DVDD; 23; Supply; Digital power supply
GPIO1/RCLK1; 26; Digital input/output; General-purpose I/O 1 or resp clock 1 (ADS1292R)
GPIO2/RCLK2; 25; Digital input/output; General-purpose I/O 2 or resp clock 2 (ADS1292R)
IN1N[(1)]; 3; Analog input; Differential analog negative input 1
IN1P[(1)]; 4; Analog input; Differential analog positive input 1
IN2N[(1)]; 5; Analog input; Differential analog negative input 2
IN2P[(1)]; 6; Analog input; Differential analog positive input 2
PGA1N; 1; Analog output; PGA1 inverting output
PGA1P; 2; Analog output; PGA1 noninverting output
PGA2N; 7; Analog output; PGA2 inverting output
PGA2P; 8; Analog output; PGA2 noninverting output
PWDN/RESET; 15; Digital input; Power-down or system reset; active low
RESP_MODN/IN3N[(1)]; 32; Analog input/output; N-side respiration excitation signal for respiration or auxiliary input 3N
RESP_MODP/IN3P[(1)]; 31; Analog input/output; P-side respiration excitation signal for respiration or auxiliary input 3P
RLDIN/RLDREF; 29; Analog input; Right leg drive input to MUX or RLD amplifier noninverting input; connect to AVDD if not used
RLDINV; 28; Analog input; Right leg drive inverting input; connect to AVDD if not used
RLDOUT; 30; Analog input; Right leg drive output
SCLK; 20; Digital input; SPI clock
START; 16; Digital input; Start conversion
VCAP1; 11; —; Analog bypass capacitor
VCAP2; 27; —; Analog bypass capacitor
VREFN; 10; Analog input; Negative reference voltage; must be connected to AVSS
VREFP; 9; Analog input/output; Positive reference voltage

[(1)]Connect unused analog inputs to AVDD.

According to the data sheet for the TI ADS1292R, the modulation signals are supplied by RESP_MODP and RESP_MODN. Exemplary modulation frequencies are 32 kHz and 64 kHz. Also, according to the data sheet for the TI ADS1292R, if the Right Arm Lead and Left Arm Lead are intended to measure respiration and ECG signals, the two leads are each wired into channel 1 for respiration signals and channel 2 for ECG signals. Accordingly, FIG. 1 depicts the Right Arm Lead wired into IN2N and IN1N and the Left Arm Lead wired into IN1P and IN2P. FIG. 1 further depicts that the Right Arm Lead is also wired into RESP_MODP and that the Left Arm Lead is also wired into RESP_MODP.

However, Applicant determined that the result of the circuit disclosed in the data sheet for the TI ADS1292R was unsatisfactory for measuring respiration with the contacts placed at a user's extremities. Thus, there is a need for a system and method for measuring a user's respiration from extremities.

BRIEF DESCRIPTION OF THE DRAWINGS

The embodiments are illustrated by way of example and not limitation in the figures of the accompanying drawings, in which like references indicate similar elements, and in which.

DETAILED DESCRIPTION

Applicant desired to measure a user's respiration and ECG signals at the user's wrist using a wrist-mounted device. For Applicant, the circuit disclosed in the data sheet for the TI ADS1292R was unsatisfactory for measuring a user's respiration at this extremity because excessive electromagnetic interference (EMI) resulted in noise in the demodulated signal. The noise was large enough to cause errors in the determination of a user's respiration rate. Applicant surmised that the ability of the human body to act as an antenna contributed to the excessive EMI and that attempting to measure respiration from an extremity (i.e., the wrist) further exacerbated the EMI.

Embodiments within disclose improved systems and methods for measuring respiration that are suitable for measuring respiration at the user's extremities. The embodiments are discussed using the Texas Instruments ADS1292R processor, but the ADS1292R is an exemplary electronics device and the systems and methods disclosed within may be practiced using other processors, processor sets, circuitry (both digital and analog), or combinations of these. Thus, "processing electronics" may include one or more processors, processor sets, circuitry (both digital and analog), or combinations of these. The improvements may include one or more of the following: 1) providing user-excitation contacts for the AC modulation signals where the user-excitation contacts are separate and distinct from user impedance-measuring contacts; 2) adding a low-pass filter between each user impedance-measuring contact and the respective input into the processing electronics; 3) adding a capacitance between the inputs into the processing electronics; 4) filtering a digital impedance signal within the processing electronics to remove a DC component; 5) filtering the digital impedance signal within the processing electronics with a low-pass filter to remove further noise; and 6) creating long and short running averages of the impedance signal and, from these, determining that the user is inhaling when the short running average is greater than the long running average and that the user is exhaling when the short running average is less than the long running average.

Figure 1:
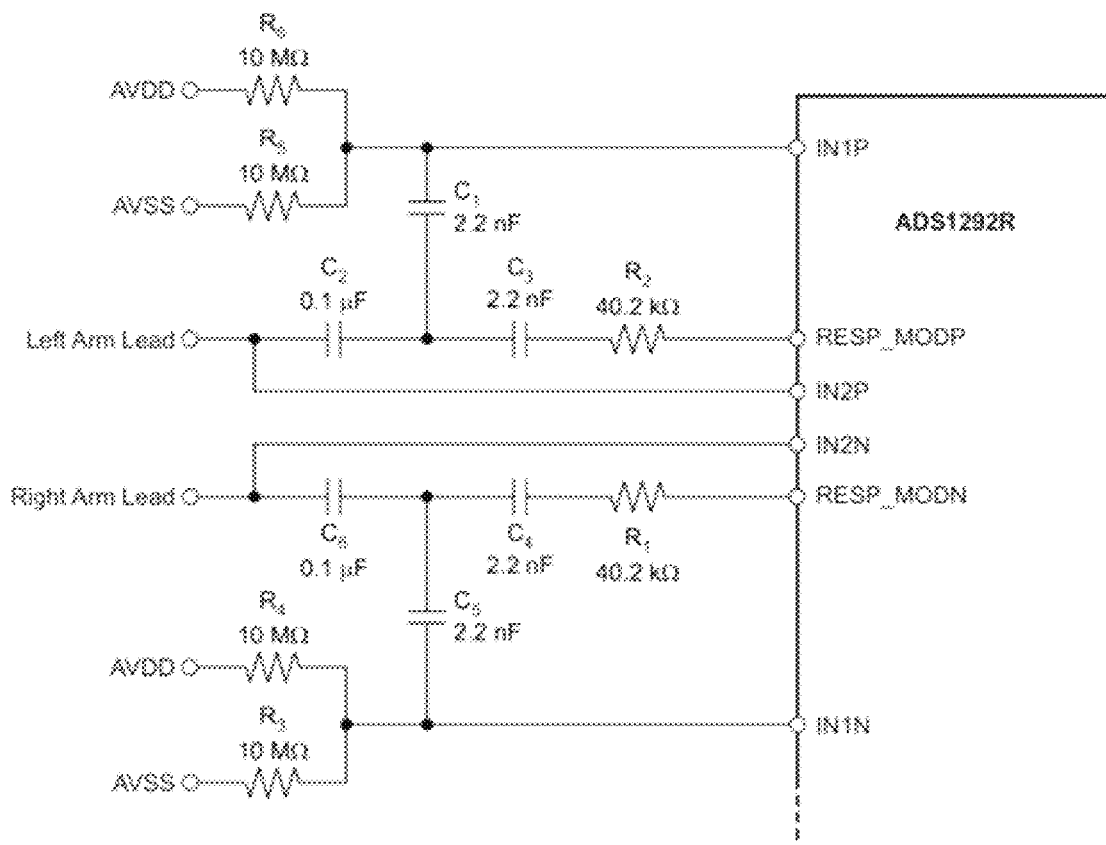
FIG. 1 is a prior art circuit diagram.
Figure 2:
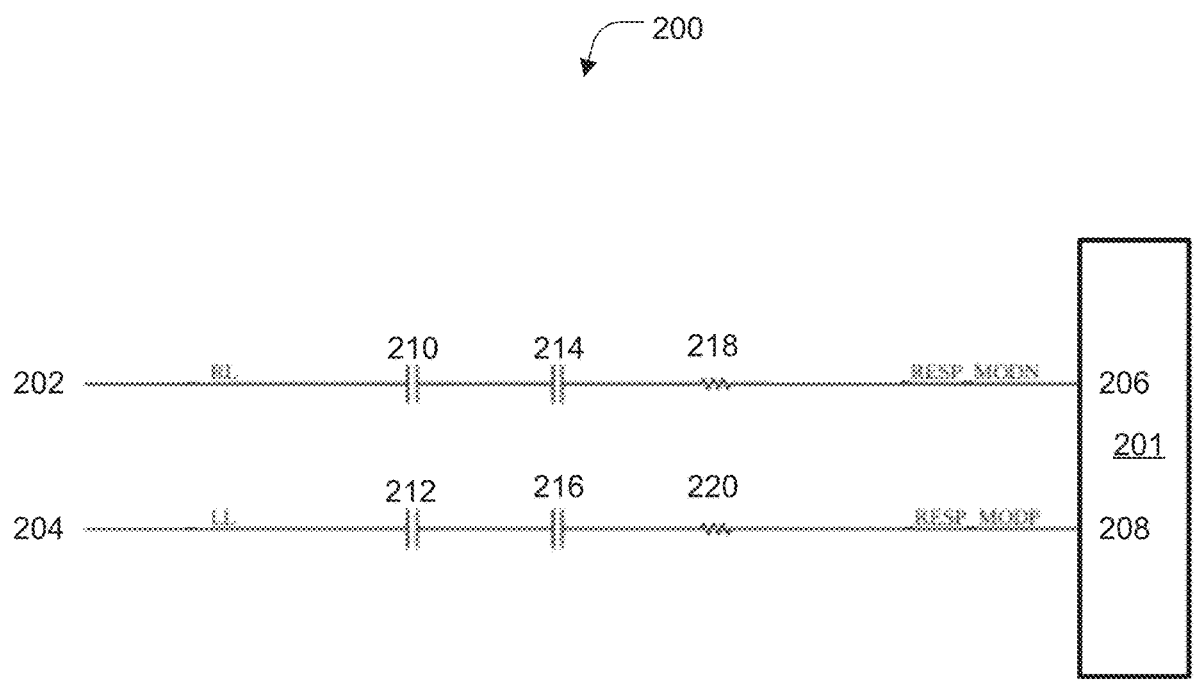
FIG. 2 is a circuit diagram illustrating aspects of an embodiment of a system for measuring the respiration of a user.
Figure 3:
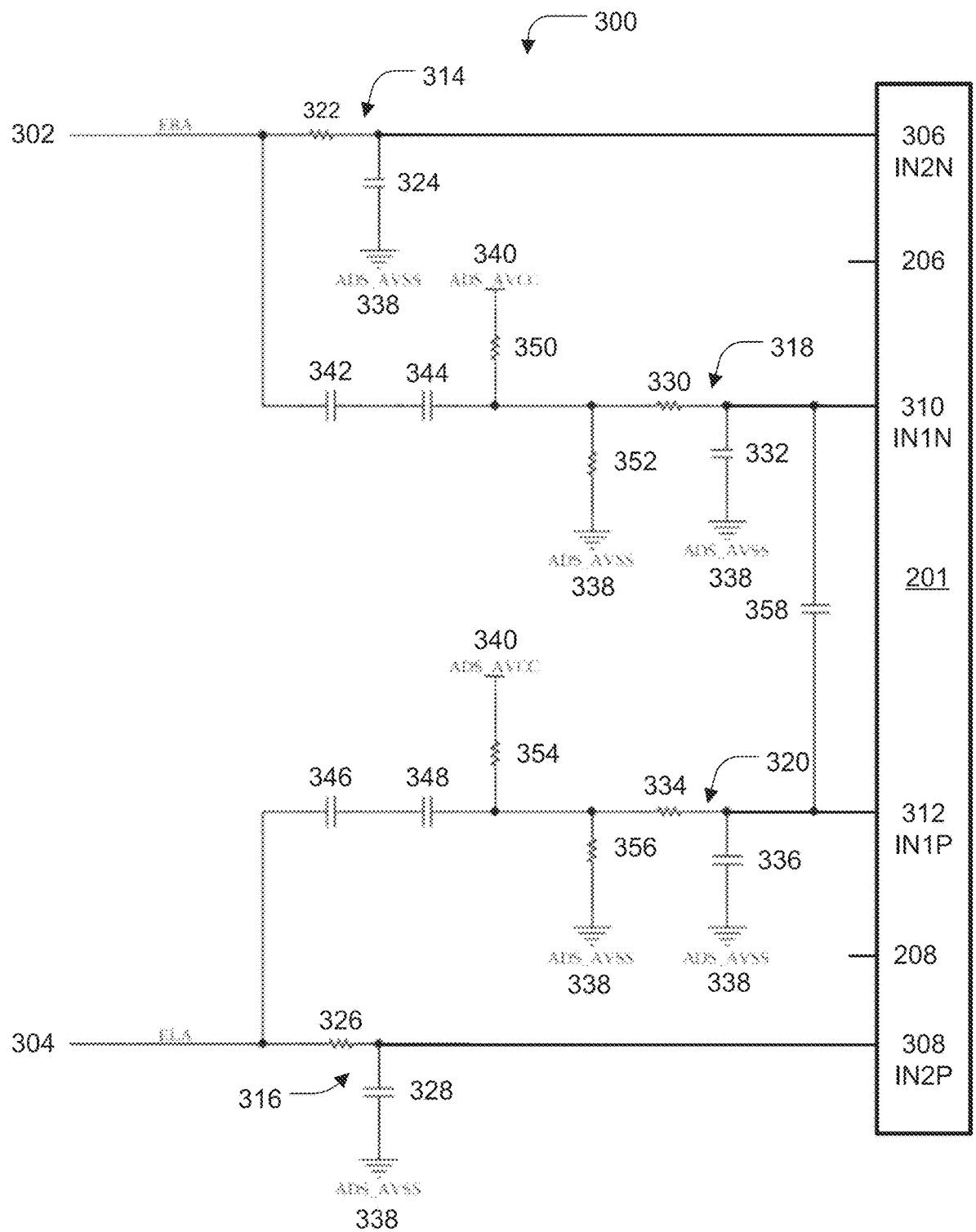
FIG. 3 is a circuit diagram further illustrating aspects of the embodiment of a system for measuring the respiration of a user of FIG. 2.

FIG. 2 and FIG. 3 are circuit diagrams illustrating aspects of an embodiment of a system for measuring a user's respiration from extremities. FIG. 2 illustrates an embodiment of a modulation circuitry 200, which provides user-excitation contacts for the AC modulation signals that are separate and distinct from user impedance-measuring contacts that are wired into the respiration channel of processing electronics 201. It was determined that providing contacts for the AC-modulation signals that are separate from the impedance-measuring contacts, by itself, significantly reduced noise (e.g., due to EMI) in the impedance measurement. In FIG. 2, modulation circuitry 200 includes a first user-excitation contact (RL) 202 coupled to a respiration modulation excitation signal source 206 from electronics 201 (e.g., a TI ADS1292R) through a capacitance and a resistance 218. In an embodiment the capacitance includes a first capacitor 210 and a second capacitor 214. In FIG. 2, a second user-excitation contact (LL) 204 is coupled to a respiration modulation excitation signal source 208 through a capacitance and a resistance 220. In an embodiment the capacitance includes a first capacitor 212 and a second capacitor 216. In the embodiment of FIG. 2, to provide AC modulation signals that result in an impedance across the user's chest, user-excitation contacts 202 and 204 are placed in contact with the skin of a user and on either side of the user's chest. In an embodiment, a contact may be made, e.g., at each wrist of the user, or at one wrist and a finger of the opposing arm. Exemplary modulation frequencies for the user-excitation signals include 32 kHz and 64 kHz. In an embodiment, resistances 218, 220 may be 40 kΩ, capacitors 210, 212 may be 100 nF, and capacitors 214, 216 may be 2200 pF.

FIG. 3 is a circuit diagram further illustrating aspects of the embodiment of a system for measuring a user's respiration from extremities of FIG. 2. FIG. 3 illustrates circuitry 300, which includes circuitry for measuring the impedance of a user at extremities using a first user-extremity contact 302 and a second user-extremity contact 304. In the embodiment of FIG. 3, to measure the impedance that results from the AC modulation signals across the user's chest, user-extremity contacts 302 and 304 are placed in contact with the skin of the user and on either side of the user's chest. In an embodiment, a contact may be made, e.g., at each wrist of the user, or at one wrist and a finger of the opposing arm. FIG. 3 further illustrates that modulation circuitry 200 is completely separate and distinct from the impedance-measuring circuitry between user contacts 302, 304 up to electronics 201. In FIG. 3, for measuring impedance, user-extremity contact 302 is coupled to an impedance-measuring input 310 to electronics 201. In this particular embodiment, input 310 is differential analog negative input 1 to the TI ADS1292R. Second user-extremity contact 304 is coupled to a second input 312 to electronics 201. In this particular embodiment, input 312 is differential analog positive input 1 to the TI ADS1292R. Between contact 302 and input 310 the circuitry further includes a capacitance, voltage biasing circuitry, and a low-pass filter 318. In this particular embodiment, the capacitance includes two capacitors 342, 344. The voltage biasing circuitry includes two resistors 350, 352, each coupled at one end between the capacitance and low-pass filter 318, with resistor 350 coupled to an analog supply voltage 340 and resistor 352 coupled to an analog ground 338. And low-pass filter 318 includes a resistor 330 coupled between the voltage biasing circuitry and input 310 and includes a capacitor 332 coupled between resistor 330 and input 310 at one end and to ground 338 at the other. Between contact 304 and input 312 the circuitry mimics that between contact 302 and input 310, further including a capacitance, voltage biasing circuitry, and a low-pass filter 320. In this particular embodiment, the capacitance includes two capacitors 346, 348. The voltage biasing circuitry includes two resistors 354, 356, each coupled at one end between the capacitance and low-pass filter 320, with resistor 354 coupled to an analog supply voltage 340 and resistor 356 coupled to an analog ground 338. And low-pass filter 320 includes a resistor 334 coupled between the voltage biasing circuitry and input 312 and includes a capacitor 336 coupled between resistor 334 and input 312 at one end and to ground 338 at the other.

In the embodiment of FIG. 3, the series capacitance (e.g., capacitors 342, 344 and 346, 348) prevents a potential DC current being applied to the user, with the redundancy of two capacitors protecting against the short-circuiting of one of the capacitors. The voltage-biasing circuitry establishes a pre-determined voltage between the two resistors (e.g., between resistors 350 and 352 and between resistors 354 and 356) that, in this embodiment, is half-way between analog ground 338 and analog supply voltage 340. Low-pass filters (e.g., low-pass filter 318 and 320) reduce EMI significantly, which contributes to the ability of the embodiment to measure a user's respiration when user-contacts 302, 304 are placed on the user's extremities. Embodiments may further include a capacitance between the impedance-sensing inputs to the electronics that is sized to reduce DC noise. In FIG. 3, such a capacitance is represented by a capacitor 358 coupled between inputs 310 and 312.

In an embodiment, the elements of circuit 300 may have the following values: capacitors 342, 346 may be 100 nF; capacitors 344, 348 may be 2200 pF; resistors 350, 352, 354, 356 may be 10 MΩ; resistors 330, 334 may be 220 kΩ; capacitors 332, 336 may be 22 pF; and capacitor 358 may be 10 pF.

Thus, in the specific embodiment of FIG. 3, low-pass filters 318, 320 have cut-off frequencies 32.9 kHz. In other embodiments, low-pass filters 318, 320 may have other cut-off frequencies and still reduce EMI sufficiently to allow measuring a user's respiration at extremities. In general, the cut-off frequencies of low-pass filters 318, 320 are chosen to narrow the band that must be filtered later by digital filters within electronics 201. By narrowing the band, digital filters with better response may be chosen. In an embodiment, the cut-off frequencies may be between thirty and thirty-five kilohertz. Thus, in an embodiment, low-pass filters 318, 320 work in combination with signal-processing logic within electronics 201 to even further reduce EMI because low-pass filters 318, 320 may have cut-off frequencies determined to work synergistically with signal-processing logic within electronics 201. In an embodiment, low-pass filters 318, 320 have cut-off frequencies chosen to reduce relatively high-frequency EMI, e.g., EMI frequencies of from 100 kHz to 1000 kHz, and the digital filtering discussed within is directed to filtering out substantially lower frequencies, e.g., with cutoff frequencies of from 0.4 Hz to 20 Hz. The hardware low-pass filters 318, 320 filter out most of the noise that comes from the user's body to the circuit and the digital filters within electronics 201 may then be optimized (e.g., with filters that have improved response times) to address board noise of substantially lower frequencies, primarily 24 Hz and 60 Hz. The two different low pass filtering systems work together to provide a usable respiration signal. Further smoothing of that signal is applied digitally as discussed within, e.g., regarding FIGS. 4-7.

FIG. 3 further illustrates an embodiment of a system for measuring a user's ECG at extremities. For reasons that are similar to those when measuring respiration at extremities, measuring a user's ECG at extremities suffers from increased EMI. In FIG. 3, circuitry 300 illustrates an embodiment of ECG-measuring circuitry for measuring the impedance of a user at extremities using first user-extremity contact 302 and second user-extremity contact 304 when user contacts 302, 304 are placed in contact with the skin of the user and on either side of the user's chest, e.g., at each wrist of the user, or at one wrist and a finger of the opposing arm. In FIG. 3, for measuring a user's ECG, a low-pass filter 314 is coupled between user-extremity contact 302 and an input 306 to electronics 201. In this particular embodiment, input 306 is differential analog negative input 2 to the TI ADS1292R chip. Low-pass filter 314 includes a resistor 322 coupled between user contact 302 and input 306 and includes a capacitor 324 coupled between resistor 322 and input 306 at one end and to ground 338 at the other. Between contact 304 and input 308 the circuitry mimics that between contact 302 and input 306, with low-pass filter 316 including a resistor 326 coupled between user contact 304 and input 308 and includes a capacitor 328 coupled between resistor 326 and input 308 at one end and to ground 338 at the other. In an embodiment, low-pass filters 314, 316 have cutoff frequencies that are chosen for anti-aliasing the signals to inputs 306, 308, which means their cutoff frequencies are substantially higher than those of low-pass filters 318, 320. For example, in an embodiment, the cutoff frequencies of low-pass filters 314, 316 may be 60,000 Hz.

In the embodiment of FIG. 2 and FIG. 3, electronics 201 includes instructions, which, when contacts 202, 204, 302, 304 are in contact with a user, cause electronics 201 to determine the impedance between user extremity contacts 302 and 304 and measure the user's respiration rate. The instructions are further discussed regarding FIGS. 4-7.

In an embodiment, electronics 201 may include a first processor and a second processor. In the embodiment, the first processor includes electronics contacts 206, 208, 310, 312. The first processor creates a digital impedance signal corresponding to analog impedance data from user contacts 302, 304 and provides the digital impedance signal to the second processor for subsequent digital signal processing. In an embodiment, the first processor may be a TI ADS1292R analog-to-digital converter and the second processor may be an Arm Cortex M4.

Figure 4:
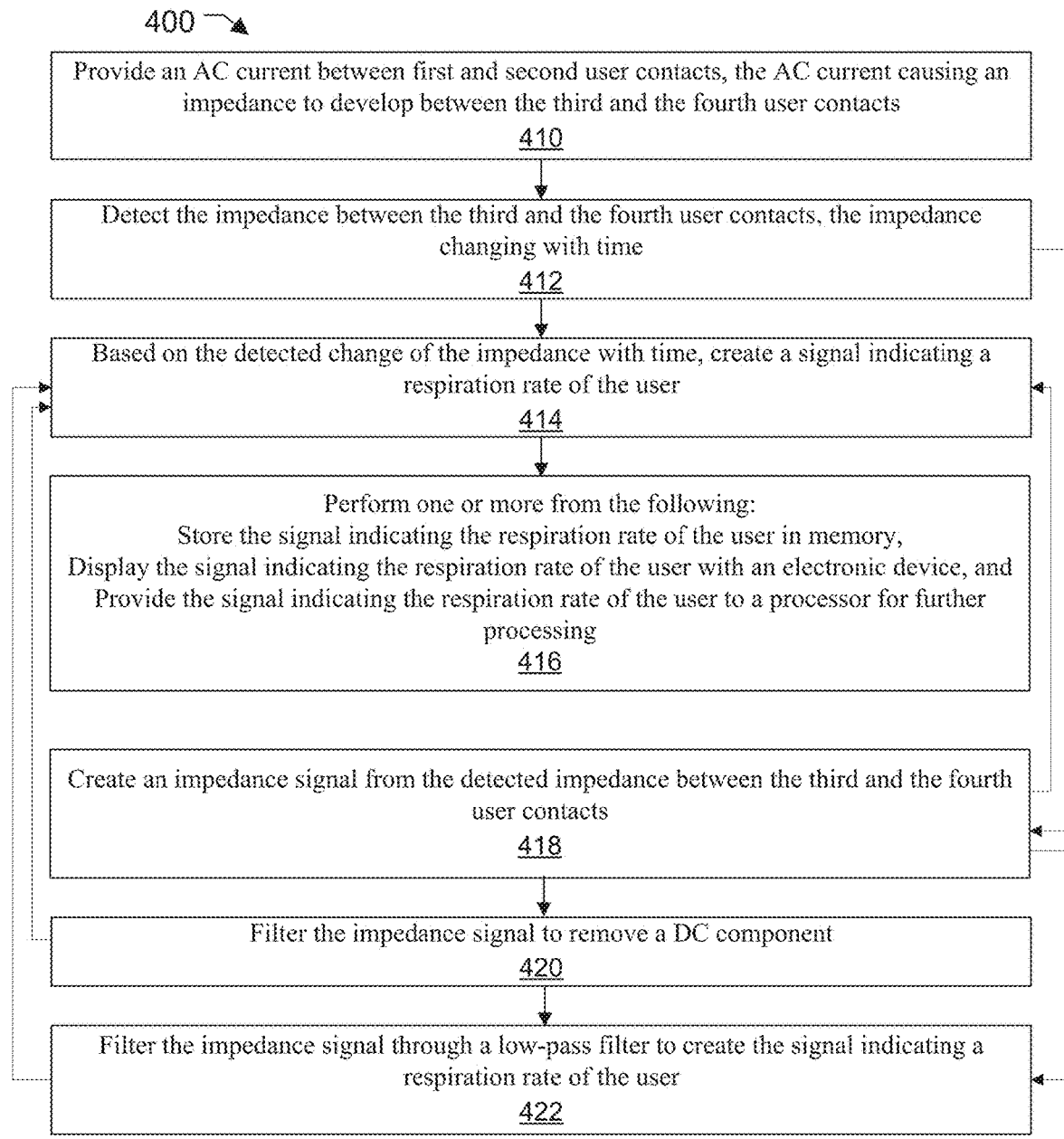
FIG. 4 illustrates an embodiment of a method for measuring the respiration of a user.

FIG. 4 illustrates an embodiment of a method 400 for measuring a user's respiration from an extremity of the user. In the embodiment, method 400 is performed with first and second user contacts on opposing sides of the user's chest and the third and fourth user contacts also on opposing sides of the user's chest. In method 400, at step 410, an AC current is provided between first and second user contacts, causing an impedance to develop between third and the fourth user contacts. In an embodiment, the contacts may be at a user's extremity, e.g., a user's wrist, or a user's finger. In step 412, the impedance is detected between the third and the fourth user contacts, the impedance changing with time due to the respiration of the user. In step 414, based on the detected change of the impedance with time, a signal is created that may be used to indicate the respiration rate of the user. The signal is created, in part, by demodulating the detected impedance to separate the contribution from the user's respiration from the contribution from the AC modulation signal. In step 416, at least one step from the following steps may be performed: the signal is stored in memory; the signal is displayed with an electronic device, and the signal is provided to a processor for further processing.

It was determined that the impedance measurement of method 400 is improved (i.e., has less noise) when performed using the embodiments of the system described regarding FIG. 2 and FIG. 3. Thus, in an embodiment, steps 410-416 may be performed using an embodiment of a system described in FIG. 2 and FIG. 3, with the embodiment providing a signal indicating a respiration rate of the user and benefitting from noise-reduction contributions provided by embodiments of the system described regarding FIG. 2 and FIG. 3.

FIG. 4 indicates additional steps, one or more of which may be added between steps 412 and 414 to assist in creating the signal that may be used to indicate the respiration rate of the user. In step 418, an impedance signal may be created from the impedance detected in step 412 between the third and the fourth user contacts. In step 420, the impedance signal may be filtered to remove a DC component, which was determined to exist even after demodulation. In an embodiment, the filtering to remove a DC component may use a digital filter. In an embodiment, the digital filter may be an infinite impulse response (IIR) filter for DC current with a filtering constant of 0.992. In step 422, the impedance signal may be filtered through a low-pass filter, e.g., to further remove EMI. In an embodiment, the low-pass filter may be a digital filter. In an embodiment, the digital low-pass filter may be a finite impulse response (FIR) low-pass filter. In an embodiment, the filter is chosen to permit frequencies associated with breathing rates, including the particularly desired (or "targeted") breathing rates. In an embodiment, the FIR may be a $179^{th}$ order filter with a gain of 1 with 5 dB from 0 to 0.5 Hz and a gain of 0 from 3 Hz and above and with −40 dB attenuation. In an embodiment, the FIR may be a $179^{th}$ order filter with a gain of 1 with 5 dB from 0 to 2 Hz and a gain of 0 from 3 Hz and above and with −40 dB attenuation. In an embodiment, the impedance signal may be filtered by a band-pass filter. In an embodiment, the band-pass filter may be a digital filter. In an embodiment, the digital band-pass filter may be a combination of the IIR filter for DC current and the FIR low-pass filter.

It was determined that steps 420, 422 are effective in reducing noise in the impedance measurement, both individually and in combination. Thus, in embodiments, one or both of steps 420, 422 may be performed with steps 410-416 to provide a signal indicating a respiration rate of the user and benefitting from noise-reduction contribution from each added step.

It was also determined that the benefits in reduced noise provided by steps 420, 422 were additive to the improvements provided using the embodiments of the system described regarding FIG. 2 and FIG. 3. Thus, in an embodiment, steps 410-416 may be performed using an embodiment of a system described in FIG. 2 and FIG. 3, with the embodiment of method and system providing a signal indicating a respiration rate of the user and benefitting from the noise-reduction contributions of step 420 or step 422 or both.

Figure 5:
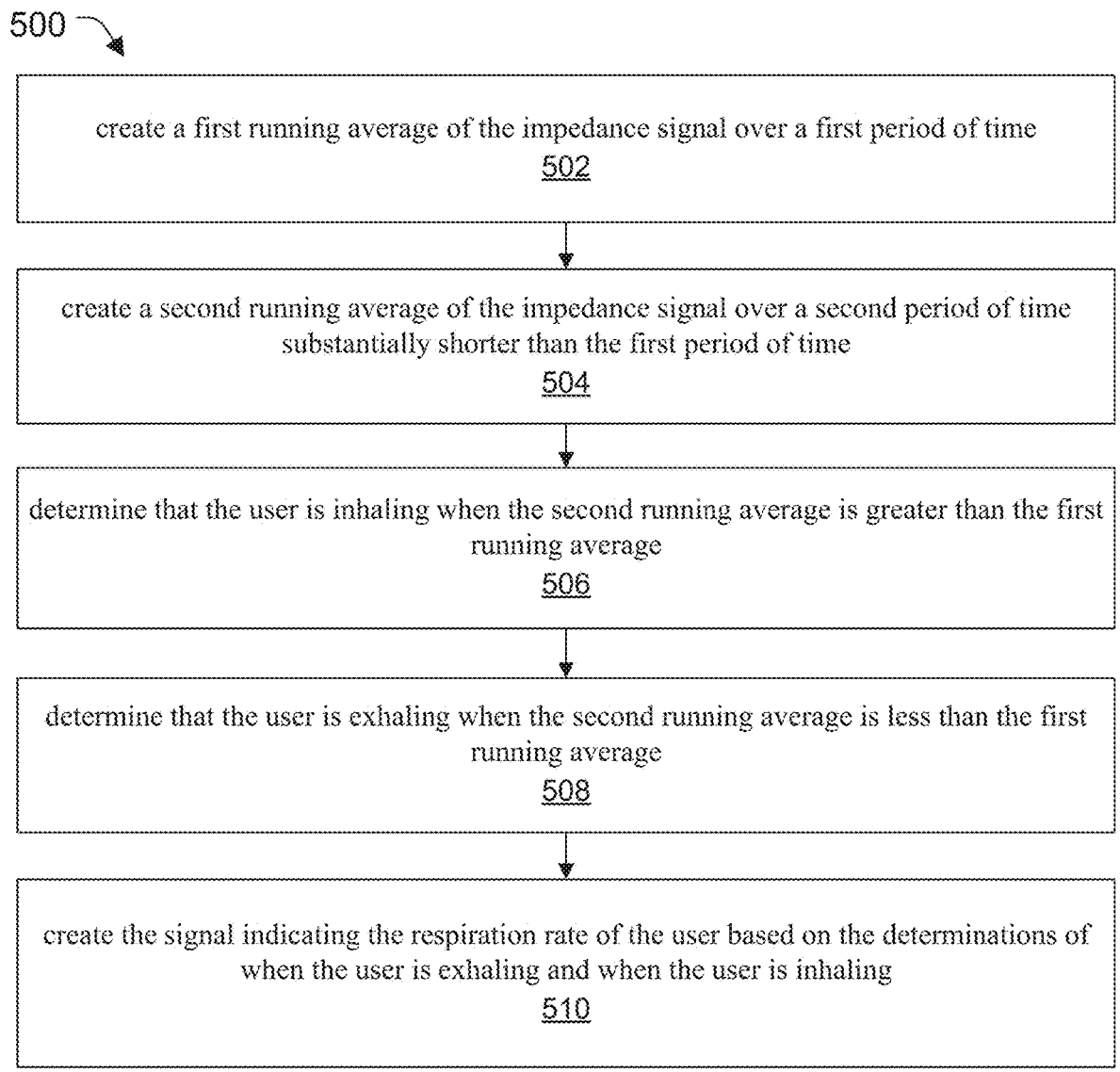
FIG. 5 illustrates an embodiment of a method for measuring the respiration of a user.

FIG. 5 illustrates an embodiment of a method 500 for measuring a user's respiration from extremities. In FIG. 500 describes steps that may be performed on an impedance signal created from the detected impedance between the third and fourth user contacts (as in any of the signals created in steps 412, 418, 420, or 422, before they are provided to step 414) from which a signal indicting a respiration rate of the user is created as in step 414. In step 502, from an impedance signal created from the time-varying impedance detected between the third and fourth user contacts, a first running average is created over a first running period of time. In step 504, from the same impedance signal of step 502, a second running average is created from a second running period of time, where the second running period of time is substantially shorter than the first running period of time. In step 506, the first and second running averages are compared and if the second running average is greater than the first, it is determined that the user is inhaling. Conversely, in step 508, if the second running average is less that the first, it is determined that the user is exhaling. In step 510, the durations of time between the determinations of when the user is inhaling and exhaling are used to create the signal indicating the respiration rate of the user.

In the embodiment of FIG. 5, the longer running average is taken over a period of time with a duration sufficient to determine the average impedance of at least one entire wave, i.e., an entire respiration cycle. This effectively provides the center amplitude of the wave (or the "baseline"). Thus, taking the longer running average is a form of a DC component filtering over and above the IIR filter mentioned earlier. In the embodiment, the shorter running average is taken over a period of time with a duration that reduces noise without filtering out the impedance change caused by the user's respiration. In an embodiment, the shorter running average is taken over a 2-second window and the longer running average is taken over an 11-second window. The shorter running average is also a form of filtering that is over and above the FIR filter mentioned earlier.

In embodiments, the methods discussed regarding FIG. 4, or FIG. 5, or both, may be performed by embodiments of systems discussed regarding FIG. 2 and FIG. 3. In embodiments, the methods of FIG. 4 and FIG. 5 may be performed by electronics 201 where electronics 201 includes a first processor and a second processor. In these embodiments, the first processor includes electronics contacts 206, 208, 310, 312. The first processor creates a digital impedance signal corresponding to analog impedance data from user contacts 302, 304 and provides the digital impedance signal to the second processor for subsequent digital signal processing. In an embodiment, the first processor may be a TI ADS1292R analog-to-digital converter and the second processor may be an Arm Cortex M4.

In an embodiment, the filtering power of low-pass filters 318, 320 is increased (or the filtering is "front loaded"), which allows the digital filtering described regarding FIG. 4 and FIG. 5 to be fine-tuned and directed to the remaining noise, thus enhancing the overall noise-reducing effect of the embodiment over changes to just the circuits 200, 300 or to just the methods 400, 500.

Figure 6:
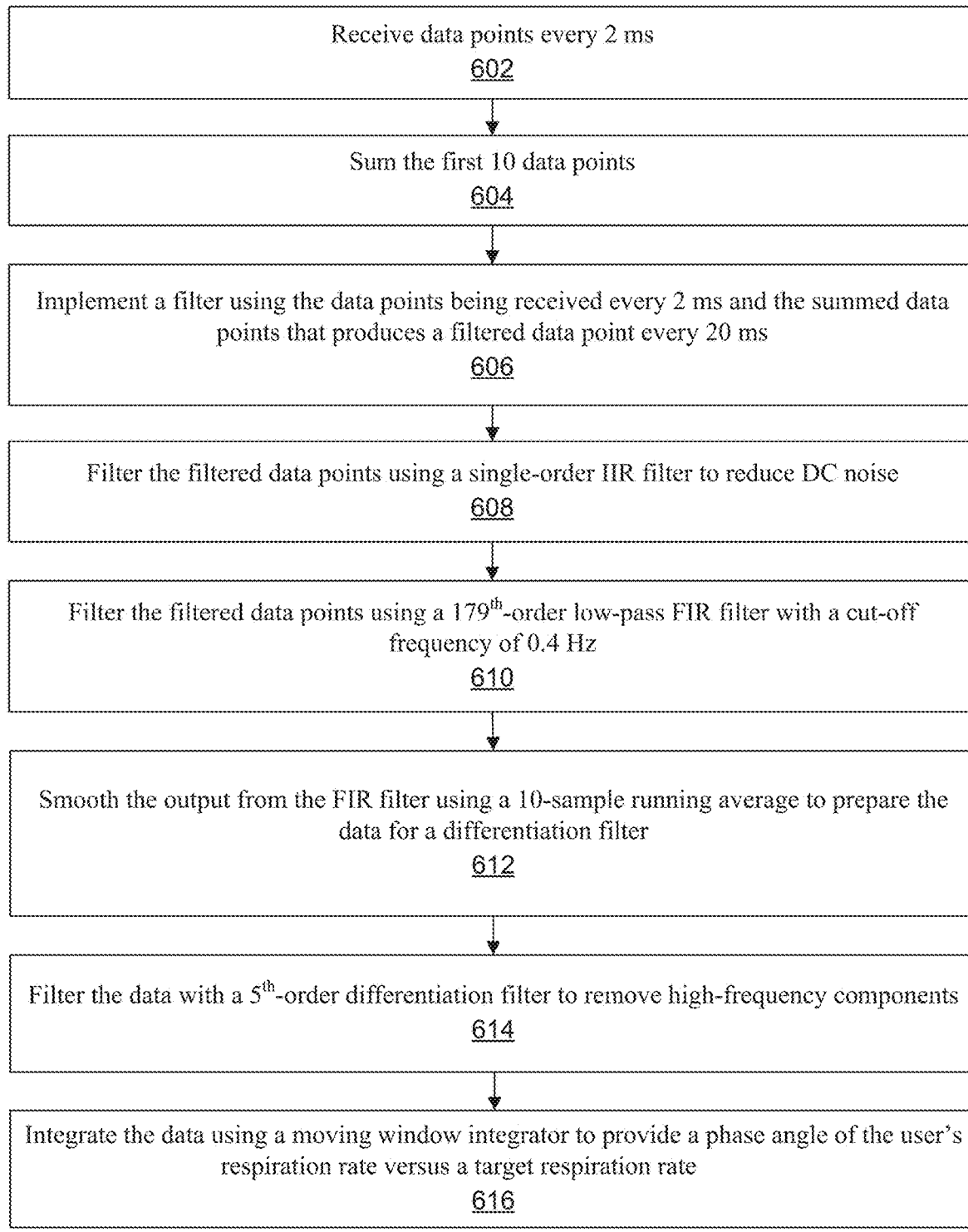
FIG. 6 illustrates an embodiment of a method for measuring the respiration of a user.

FIG. 6 illustrates an embodiment of a method 600 for measuring the respiration of a user. The embodiment of FIG. 6 is directed to processing that may be performed on a digital signal created from the changes in impedance caused by a user's respiration, e.g., a digital signal created from the impedance from step 412 of method 400, or a digital impedance signal created by electronics 201 and further processed by software within electronics 201. In FIG. 6, in step 602, a data point indicative of an impedance is received (or taken) at a pre-determined frequency, e.g., every 2 ms (i.e., the sampling rate is 500 Hz). In step 604, a pre-determined number of data points are summed, e.g., 10 data points may be summed. In step 606, after the data points are summed, a filter is implemented that produces a filtered data point at a predetermined frequency, e.g., every 20 ms (i.e., 50 Hz). In step 608, a single-order IIR filtering is performed on the data from step 606 to reduce DC noise. In an embodiment, this IIR filter is an IIR filter from Texas Instruments included with the TI ADS1292R digital-to-analog converter. In step, 610, the data stream from step 608 is further filtered using a low-pass FIR filter, e.g., a $179^{th}$-order low-pass FIR filter with a cut-off frequency of 0.4 Hz. With the data being sampled at a sufficiently high frequency, e.g., 50 Hz, an FIR filter may be employed with such a low cut-off frequency without the number of taps being too large for the processor to accommodate (i.e., a lower-order FIR filter). In step 612, a running average, e.g., a 10-sample running average, is used to smooth the output from the FIR filter and prepare the data for a differentiation filter. In step 614, the data is filtered with a differentiation filter, e.g., a $5^{th}$-order differentiation filter, which removes high-frequency components from the data. If the output of step 614 is larger than 0, then the user is determined to be inhaling. Otherwise the user is exhaling. In step 616, the data is integrated using a moving window integrator with, e.g., a 50-sample window, which at this sampling rate is 1 second of data. The output of step 616 may be used to compare the phase angle of the user's respiration with a target respiration. In an embodiment, the user's respiration rate may be determined using the time between zero-transitions with the data from step 614. In an embodiment, the determined user respiration rate may be compared to the changes in the user's HRV to determine whether the user's HRV is in synchrony with the user's respiration (i.e., whether the user is in RSA). In an embodiment, the signal from step 412 may be processed as described in steps 608-614 with the resulting signal supplied to step 414. In an embodiment, the signal from step 412 may be processed as described in steps 602-614 with the resulting signal supplied to step 414.

Figure 7:
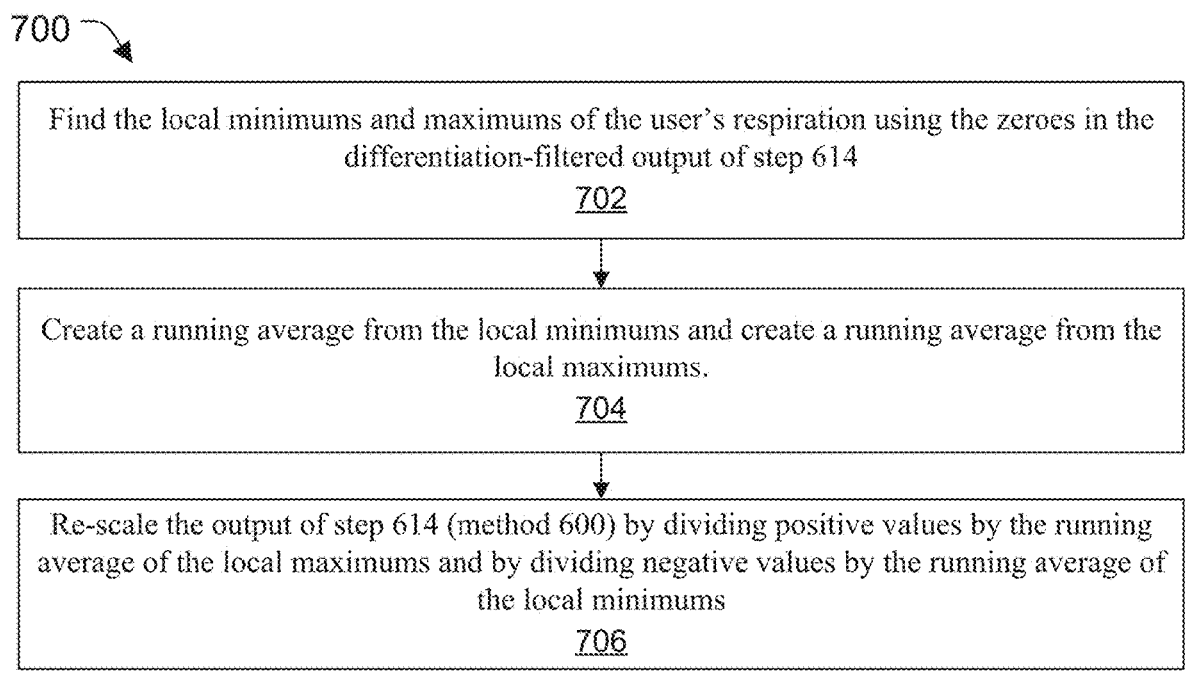
FIG. 7 illustrates an embodiment of a method for measuring the respiration of a user.

FIG. 7 illustrates an embodiment of a method 700 for measuring the respiration of a user that corrects for (or "cancels out") skewing that might be induced due the user's skin varying in a level of moistness while respiration is being measured. Method 700 builds on method 600. In step 702, the zeroes in the differentiation-filtered output of step 614 are used to find the local minimums and maximums of the user's respiration. In step 704, a running average is created from the local minimums and a running average is created from the local maximums. In step 706, the output of step 614 is rescaled by dividing positive values by the running average of the local maximums and by dividing negative values by the running average of the local minimums. The result of step 706 is that the respiration data will be a scaled wave that ranges from −1 to 1, where positive values indicate the user is inhaling and negative values indicate the user is exhaling. With the respiration data being maintained between −1 and 1, the skew is eliminated. In an embodiment, the running average of step 704 is constructed using the last ten (10) local minimums and last ten (10) local maximums.

Figure 8:
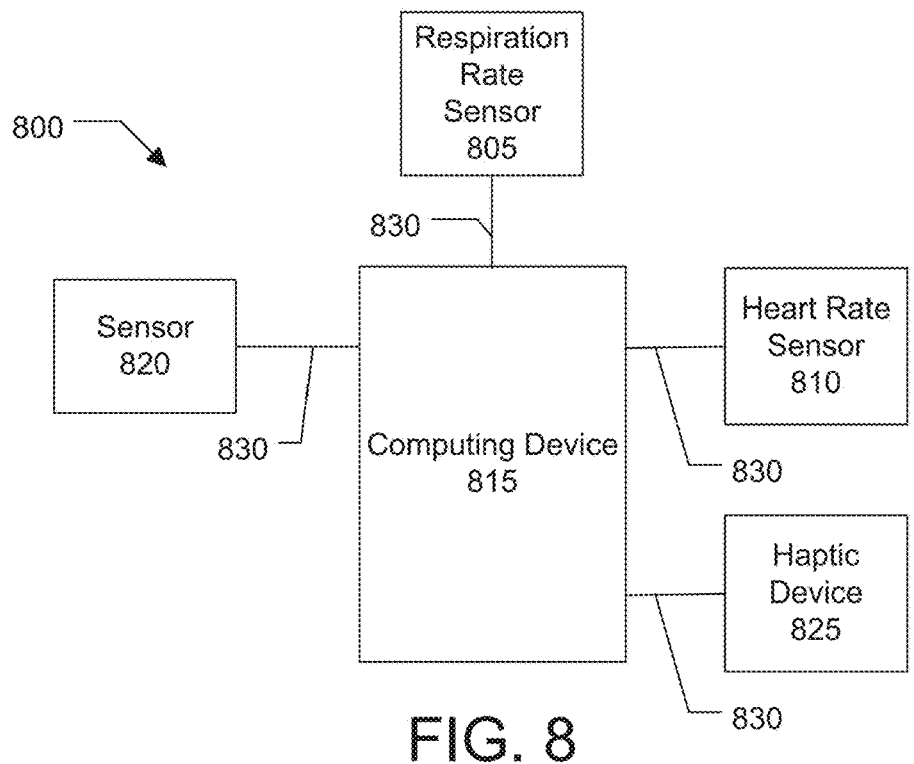
FIG. 8 is a simplified, exemplary block diagram of an embodiment of a system for measuring the respiration of a user.

FIG. 8 is a simplified, exemplary block diagram of an embodiment of a system 800 for implementing the embodiments of systems and methods disclosed herein. System 800 may include a number of sensors, e.g., a respiration rate sensor 805 (e.g., as described within this disclosure) and a heart rate sensor 810 (e.g., as described within this disclosure), for developing data regarding a user. Sensors 805, 810, and 820 are in communication with a computing device 815. Computing device 815 may further be in control of a haptic device 825 and a buzzer or speaker (not shown) for communicating with the user. System 800 may be referred to as a Biometric Analysis Device.

Respiration rate sensor 805 may be an impedance-based sensor as discussed within this specification. Heart rate sensor 810 may be, e.g., a plurality of sensors sufficient to produce an electrocardiogram (ECG, as discussed within), a chest-mounted device, or a wrist-mounted device, so long as the device provides heart rate data with sufficient accuracy and precision. Sensor 820 is representative of additional sensors that may be included, such as sensors for determining galvanic skin response, temperature, blood pressure, hydration, sleep, exercise activity, brain activity, nutrient levels, or blood analysis. Sensors 805, 810, and 820 may supply data to computing device 815 via communication links 830.

Computing device 815 may include a user interface and software, which may implement the steps of the methods disclosed within. Computing device 815 may receive data from sensors 805, 810, and 820, via communication links 830, which may be hardwire links, optical links, satellite or other wireless communications links, wave propagation links, or any other mechanisms for communication of information. Various communication protocols may be used to facilitate communication between the various components shown in FIG. 8. Distributed system 800 in FIG. 8 is merely illustrative of an embodiment and does not limit the scope of the systems and methods as recited in the claims. In an embodiment, the elements of system 800 are incorporated into a single, wearable Biometric Analysis Device (e.g., as described regarding FIGS. 10 and 11). One of ordinary skill in the art would recognize other variations, modifications, and alternatives. For example, more than one computing device 815 may be employed. As another example, sensors 805, 810, and 820 may be coupled to computing device 815 via a communication network (not shown) or via some other server system.

Computing device 815 may be responsible for receiving data from sensors 805, 810, and 820, performing processing required to implement the steps of the methods, and for interfacing with the user. In some embodiments, computing device 815 may receive processed data from sensors 805, 810, and 820. In some embodiments, the processing required is performed by computing device 815. In such embodiments, computing device 815 runs an application for receiving user data, performing the steps of the method, and interacting with the user. In other embodiments, computing device 815 may be in communication with a server, which performs the required processing, with computing device 815 being an intermediary in communications between the user and the processing server.

System 800 enables users to access and query information developed by the disclosed methods. Some example computing devices 815 include desktop computers, portable electronic devices (e.g., mobile communication devices, smartphones, tablet computers, laptops) such as the Samsung Galaxy Tab®, Google Nexus devices, Amazon Kindle®, Kindle Fire®, Apple iPhone®, the Apple iPad®, Microsoft Surface®, the Palm Pre™, or any device running the Apple iOS®, Android® OS, Google Chrome® OS, Symbian OS®, Windows Mobile® OS, Windows Phone, BlackBerry® OS, Embedded Linux, Tizen, Sailfish, webOS, Palm OS® or Palm Web OS®; or wearable devices such as smart watches, smart fitness or medical bands, and smart glasses.

Figure 9:
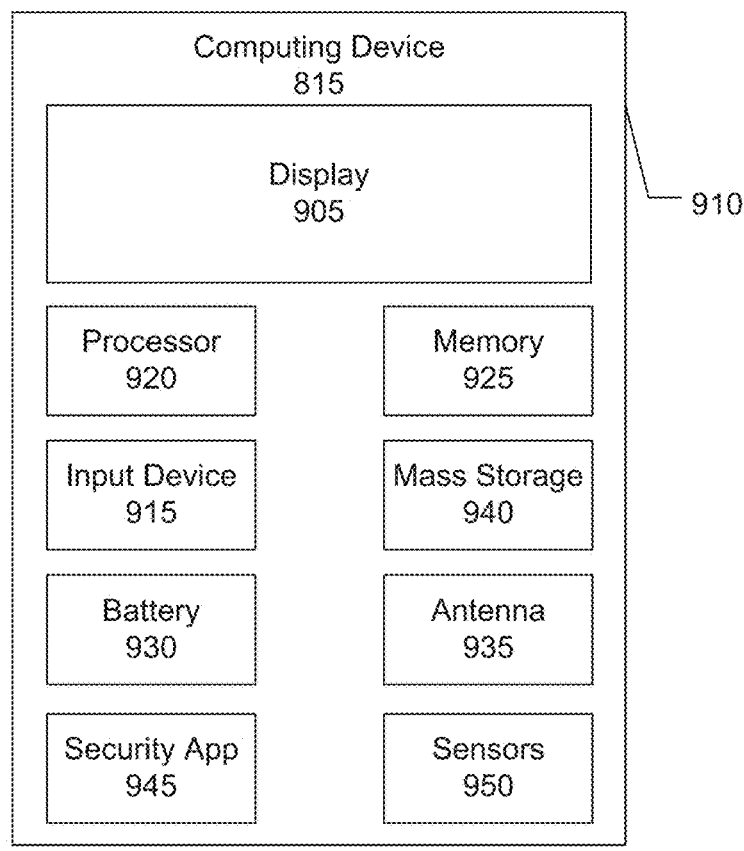
FIG. 9 is an exemplary block diagram of a computing device from the system of FIG. 8.

FIG. 9 is an exemplary block diagram of a computing device 815 from the system of FIG. 8. In an embodiment, a user interfaces with the system through computing device 815, which also receives data and performs the computational steps of the embodiments. Computing device 815 may include a display, screen, or monitor 905, housing 910, input device 915, sensors 950, and a security application 945. Housing 910 houses familiar computer components, some of which are not shown, such as a processor 920, memory 925, battery 930, speaker, transceiver, antenna 935, microphone, ports, jacks, connectors, camera, input/output (I/O) controller, display adapter, network interface, mass storage devices 940, and the like. In an embodiment, sensors 950 may include sensors 805, 810, and 820 incorporated into computing device 815, and haptic device 825 may also be incorporated into device 815. In an embodiment, housing 910 is the housing of the wearable biometric analysis device 1000 of FIGS. 10 and 11.

Input device 915 may also include a touchscreen (e.g., resistive, surface acoustic wave, capacitive sensing, infrared, optical imaging, dispersive signal, or acoustic pulse recognition), keyboard (e.g., electronic keyboard or physical keyboard), buttons, switches, stylus, or combinations of these.

Display 904 may include dedicated LEDs for providing directing signals and feedback to a user.

Mass storage devices 940 may include flash and other nonvolatile solid-state storage or solid-state drive (SSD), such as a flash drive, flash memory, or USB flash drive. Other examples of mass storage include mass disk drives, floppy disks, magnetic disks, optical disks, magneto-optical disks, fixed disks, hard disks, CD-ROMs, recordable CDs, DVDs, recordable DVDs (e.g., DVD-R, DVD+R, DVD-RW, DVD+RW, HD-DVD, or Blu-ray Disc), battery-backed-up volatile memory, tape storage, reader, and other similar media, and combinations of these.

System 900 may also be used with computer systems having configurations that are different from computing device 815, e.g., with additional or fewer subsystems. For example, a computer system could include more than one processor (i.e., a multiprocessor system, which may permit parallel processing of information) or a system may include a cache memory. The computing device 815 shown in FIG. 9 is but an example of a computer system suitable for use. For example, in a specific implementation, computing device 815 is a wrist-mounted Biometric Analysis Device in communication with or incorporating the sensors of FIG. 9. An example of such a Biometric Analysis Device is discussed regarding device 1000 of FIGS. 10 and 11. Other configurations of subsystems suitable for use will be readily apparent to one of ordinary skill in the art. In other specific implementations, computing device 815 is a mobile communication device such as a smartphone or tablet computer. Some specific examples of smartphones include the Droid Incredible and Google Nexus One®, provided by HTC Corporation, the iPhone® or iPad®, both provided by Apple, BlackBerry Z10 provided by BlackBerry (formerly Research In Motion), and many others. The Biometric Analysis Device may be a laptop or a netbook. In another specific implementation, the Biometric Analysis Device is a non-portable computing device such as a desktop computer or workstation.

In an embodiment, system 900 may be incorporated into a single module. The module may have four user contacts (or "electrodes") placed to allow a user to make contact with two contacts with one user extremity and with the other two contacts with the other user extremity. This module can be contained within numerous types of wristband straps (leather, etc.) and form factors (such as key chain, steering wheel cover, etc.). The module, or the strap or other form factor, may also include a small OLED display to display the current time. The module may execute software that performs an embodiment of the method. Accordingly, the module may provide the user with feedback, e.g., an indication of the user's respiration rate or heart rate or both.

Figure 10:
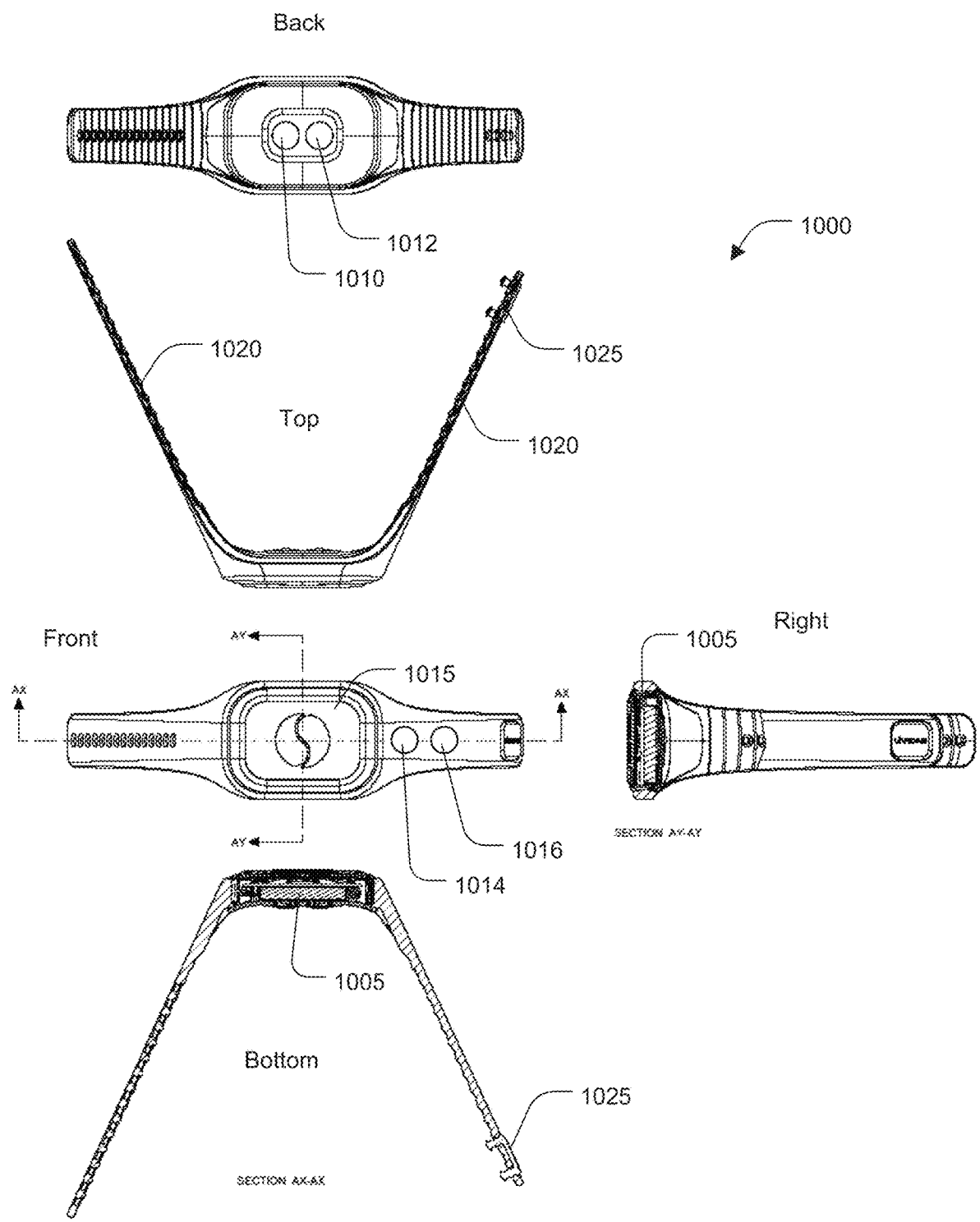
FIG. 10 includes front, back, top, bottom, and right views of an embodiment of a biometric analysis device implementing embodiments of the systems and methods disclosed herein.

FIG. 10 includes front, back, top, bottom, and right views of an embodiment of a wearable biometric analysis device 1000 for implementing embodiments of the methods disclosed within. Components and capabilities of biometric analysis device 1000 are also described with reference to FIGS. 2-9. Biometric Analysis Device 1000 includes a computing device 1005 and a sensor coupled to electrical contacts 1010, 1012, 1014, 1016 that acquire data that may be used to provide a measure of the user's respiration rate as discussed above. Computing device 1005 processes biometric data measured by the sensor(s) and produces feedback correlating to the processed biometric data. By continuously monitoring one or more biometric values, the user may respond to the data received and modify their behavior or activity to improve health and performance. The biometric analysis device 1000 thereby provides feedback by sensing and reporting a biometric value measured by the sensor to the user in real time. In an embodiment, contacts 1010, 1012, 1014, 1016 provide data to a TI ADS1292R sensor. As such, Biometric Analysis Device 1000 may be equipped with both a respiration rate sensor and a heart rate sensor. Computing device 1005 is in communication with the sensor or sensors associated with contacts 1010, 1012, 1014, 1016. Computing device 1005 may also control a haptic device (not shown) for communicating with the user. Computing device 1005 may include a display 1015, a user interface, and software, for implementing the steps of the methods disclosed within. In an embodiment, contacts 1010 and 1012 may correspond to contacts 202 and 302 as described above, and contacts 1014 and 1016 may correspond to contacts 204 and 304 as described above. In the embodiment, a method for determining the user's respiration rate includes the user placing device 1000 on one of the user's wrists such that contacts 1010, 1012 are in contact with the user's wrist. Then, the user brings contacts 1014, 1016 in contact with another part of the user's body such as one or more fingers on the user's opposing hand. In other words, the user touches contacts 1014, 1016 to a part of the user's body so that some or all of the user's chest is between contact pairs 1010, 1012 and 1014, 1016 (the circuits are described with reference to FIGS. 2 and 3 and contact pairs 202, 302 and 204, 304). In an embodiment, the part of the user's body may be a finger or other part of the opposing arm, may be a section of the user's torso, or may be a section of a leg of the user. With both contact pairs 1010, 1012 and 1014, 1016 in such contact with the user, the device then determines the user's respiration rate, heart rate, or both according to the methods described within.

Computing device 1005 may receive data from sensors 1010, 1012, 1014, 1016, perform processing required to implement the steps of the methods disclosed within, and provide a user interface via display 1015. In some embodiments, all processing required is performed by computing device 1005. In such embodiments, computing device 1005 executes instructions for receiving user data, performing the steps of the method, and interacting with the user. In other embodiments, computing device 1005 may be in communication with a server, which performs part of the required processing, with computing device 1005 being an intermediary in communications between the user and the processing server.

As illustrated, Biometric Analysis Device 1000 generally comprises a band 1020 configured to be worn about a wrist of the user. The band 1020 includes an adjustment mechanism 1025, for adjusting a circumference of the band 1020. A user can thus select, using adjustment mechanism 1025, a particular size for positioning band 1020 about the user's wrist. A visual indication, e.g., for feedback, may be provided by display 1015. In an embodiment, visual indicators may be further be positioned on the band 1020 to provide visual signals to the user. Sensor(s) associated with contacts 1010, 1012, 1014, 1016 may be configured to be activated by computing device 1005. In an embodiment, additional sensors, e.g., a temperature sensor or a galvanic response sensor, may be provided to provide more user data for determining vagal tone. In an embodiment, one or more translucent windows may be positioned about the band 1020 to transmit light from one or more indicators positioned with the band 1020.

Biometric analysis device 1000, in one embodiment, is used measure a user's respiration rate. Accordingly, the biometric analysis device 1000 may provide the user with real-time, personal biofeedback. In an embodiment, device 1000 may measure both a user's respiration rate and heart rate and provide feedback regarding one or both. The biofeedback may allow the user to learn about the user's personal physiological state and physiological responses. As a result, the biofeedback provided to the user (by, e.g., one or more of display 1015, or haptic device, or speaker) may enable the user to self-regulate the user's activity and behavior to improve the user's performance or health. In an embodiment, device 1000 may provide a user with feedback (e.g., a vibration pattern of frequency, duration, and magnitude) selected to encourage a desired behavior. In an embodiment, biometric analysis device 1000 is configured to provide the user with feedback with reference to previously-collected biometric data, such as respiration rate or heart rate variability. The biometric analysis device 1000 may emit vibrations based on the user's actual respiration rate, or a target respiration rate. For example, a visual indication from, e.g., display 1015, may be provided and configured to emit different colors based on when the user is supposed to inhale and exhale for deep breathing relaxation techniques. The user may also be capable of changing the breathing intervals. The visual indication and breathing intervals may be enabled and adjusted through the user interface.

Figure 11:
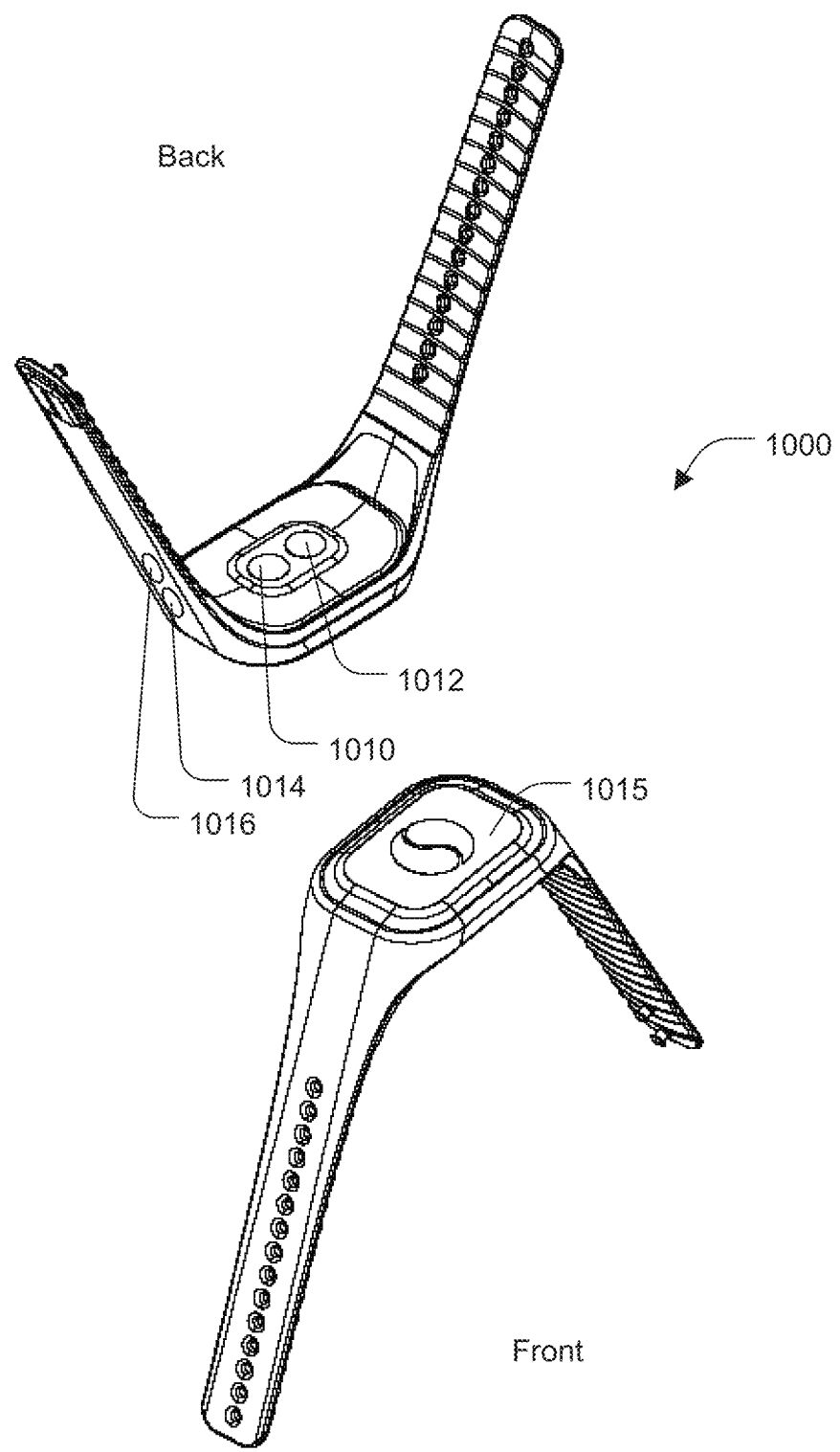
FIG. 11 is a perspective view of the biometric analysis device of FIG. 10.

FIG. 11 is a perspective view of the biometric analysis device of FIG. 10.

FIGS. 10 and 11 illustrate one example embodiment of a wearable biometric analysis device 1000 that is configured to measure the respiration rate of a user. In one embodiment, biometric analysis device 1000 can include each of the elements of system 800 of FIG. 8 and FIG. 9. In other embodiments, biometric analysis device 1000 can include other elements that function with biometric analysis device 1000 to provide biometric measurement and analysis to assist a user with stress management.

In the description above and throughout, numerous specific details are set forth in order to provide a thorough understanding of an embodiment of this disclosure. It will be evident, however, to one of ordinary skill in the art, that an embodiment may be practiced without these specific details. In other instances, well-known structures and devices are shown in block diagram form to facilitate explanation. The description of the preferred embodiments is not intended to limit the scope of the claims appended hereto. Further, in the methods disclosed herein, various steps are disclosed illustrating some of the functions of an embodiment. These steps are merely examples and are not meant to be limiting in any way. Other steps and functions may be contemplated without departing from this disclosure or the scope of an embodiment.

We claim:

1. A system comprising:
   electronics including a processor with memory and instructions and a plurality of electronics contacts for connecting with circuitry external to the electronics;
   a first user contact coupled to a first electronics contact with a first capacitor coupled between the first user contact and the first electronics contact;
   a second user contact coupled to a second electronics contact with a second capacitor coupled between the second user contact and the second electronics contact;
   a third user contact coupled to a third electronics contact with a first low-pass filter coupled between the third user contact and the third electronics contact;
   a fourth user contact coupled to a fourth electronics contact with a second low-pass filter coupled between the fourth user contact and the fourth electronics contact; and
   the instructions, when executed by the processor and when the first, second, third, and fourth user contacts are in contact with a user, causing the electronics to:
   provide an AC current between the first and second user contacts, the AC current causing an impedance to develop between the third and the fourth user contacts;
   detect the impedance between the third and the fourth user contacts, the impedance changing with time; and
   based on the detected change of the impedance with time, create a signal indicating a respiration rate of the user.

2. The system of claim 1 wherein:
   the first and second low-pass filters have a cutoff frequency of between thirty and thirty-five kilohertz; and
   a third capacitor is coupled between the third electronics contact and the fourth electronics contact and is sized to reduce direct-current noise between the third and fourth electronics contacts.

3. The system of claim 1 wherein:
   the first and second low-pass filters have cutoff frequencies to reduce electromagnetic interference; and
   a third capacitor is coupled between the third electronics contact and the fourth electronics contact and is sized to reduce direct-current noise between the third and fourth electronics contacts.

4. The system of claim 1 further comprising a third capacitor coupled between the third electronics contact and the fourth electronics contact.

5. The system of claim 4, wherein:
   the first low-pass filter includes a first resistor coupled between the third user contact and the third electronics contact and a fourth capacitor coupled to ground between the first resistor and the third electronics contact; and
   the second low-pass filter includes a second resistor coupled between the fourth user contact and the fourth electronics contact and a fifth capacitor coupled to ground between the second resistor and the fourth electronics contact, the system further comprising:

a third resistor coupled between the first capacitor and the first electronics contact;

a fourth resistor coupled between the second capacitor and the second electronics contact;

a sixth capacitor coupled between the third user contact and the first low-pass filter;

a fifth resistor coupled to a supply voltage and between the sixth capacitor and the first low-pass filter;

a sixth resistor coupled to ground and between the sixth capacitor and the first low-pass filter;

a seventh capacitor coupled between the fourth user contact and the second low-pass filter;

a seventh resistor coupled to the supply voltage and between the seventh capacitor and second low-pass filter; and an eighth resistor coupled to ground and between the seventh capacitor and the second resistor.

6. The system of claim 1 incorporated into a wrist-mountable device configured to position the first and third user contacts against a wrist of a first arm of the user and to provide access for the user to make contact with the second and fourth user contacts with a part of a second arm of the user.

7. The system of claim 1, wherein the instructions for creating a signal indicating a respiration rate of the user further cause the electronics to:
create an impedance signal from the detected impedance between the third and the fourth user contacts;
filter the impedance signal to remove a DC component; and
filter the impedance signal through a third low-pass filter to create the signal indicating a respiration rate of the user.

8. The system of claim 7, wherein the third low-pass filter has a cut-off frequency of two hertz and the attenuation is minus forty decibels per decade above three hertz.

9. The system of claim 7, the instructions further causing the electronics to:
create a first running average of the impedance signal over a first period of time;
create a second running average of the impedance signal over a second period of time substantially shorter than the first period of time;
determine that the user is inhaling when the second running average is greater than the first running average;
determine that the user is exhaling when the second running average is less than the first running average; and
create the signal indicating the respiration rate of the user based on the determinations of when the user is exhaling and when the user is inhaling.

10. The system of claim 1, wherein the electronics includes a Texas Instruments ADS1292R analog-to-digital converter and an Arm Cortex M4 processor and the first through fourth electronics contacts are on the Texas Instruments ADS1292R analog-to-digital converter.

11. A wrist-mountable device including:
electronics including a processor with memory and instructions;
a first user contact configured to be positioned against a first arm of a user;
a second user contact configured to be accessed by a part of a second arm of the user;
a third user contact configured to be positioned against the first arm of the user; and a fourth user contact configured to be accessed by a part of a second arm of the user, wherein the instructions, when executed by the processor and when the first, second, third, and fourth user contacts are in contact with the user, cause the electronics to:
provide an AC current between the first and second user contacts, the AC current causing an impedance to develop between the third and the fourth user contacts;
create an impedance signal from a detected impedance between the third and the fourth user contacts, the impedance changing with time;
filter the impedance signal to remove a DC component and filter the impedance signal through a low-pass filter to create a filtered impedance signal;
create a first running average of the filtered impedance signal over a first period of time;
create a second running average of the filtered impedance signal over a second period of time substantially shorter than the first period of time;
determine that the user is inhaling when the second running average is greater than the first running average;
determine that the user is exhaling when the second running average is less than the first running average; and
create a signal indicating a respiration rate of the user based on the determinations of when the user is exhaling and when the user is inhaling.

12. The device of claim 11, wherein the low-pass filter has a cut-off frequency of two hertz and the attenuation is minus forty decibels per decade above three hertz.

13. The device of claim 11, wherein the electronics includes a Texas Instruments ADS1292R analog-to-digital converter and an Arm Cortex M4 processor and the first through fourth electronics contacts are on the Texas Instruments ADS1292R analog-to-digital converter.

14. A wrist-mountable device including:
electronics including a processor with memory and instructions;
a first user contact configured to be positioned against a first arm of a user;
a second user contact configured to be accessed by a part of a second arm of the user;
a third user contact configured to be positioned against the first arm of the user; and
a fourth user contact configured to be accessed by a part of the second arm of the user;
a first electronics contact coupled to the first user contact with a first capacitor in series between the first user contact and the first electronics contact;
a second electronics contact coupled to the second user contact with a second capacitor in series between the second user contact and the second electronics contact;
a third electronics contact coupled to the third user contact with a first low-pass filter coupled between the third user contact and the third electronics contact; and
a fourth electronics contact coupled to the fourth user contact with a second low-pass filter coupled between the fourth user contact and the fourth electronics contact, wherein the instructions, when executed by the processor and when the first, second, third, and fourth user contacts are in contact with the user, cause the electronics to:
provide an AC current between the first and second user contacts, the AC current causing an impedance to develop between the third and the fourth user contacts;

detect the impedance between the third and the fourth user contacts, the impedance changing with time; and based on the detected change of the impedance with time, create a signal indicating a respiration rate of the user.

15. The device of claim 14, wherein:

the first and second low-pass filters have a cutoff frequency of between thirty and thirty-five kilohertz; and a third capacitor is coupled between the third electronics contact and the fourth electronics contact and is sized to reduce direct-current noise between the third and fourth electronics contacts.

16. The device of claim 14, wherein:

the first and second low-pass filters have cutoff frequencies to reduce electromagnetic interference; and a third capacitor is coupled between the third electronics contact and the fourth electronics contact and is sized to reduce direct-current noise between the third and fourth electronics contacts.

17. The device of claim 14 further comprising a third capacitor coupled between the third electronics contact and the fourth electronics contact.

18. The device of claim 17, wherein:

the first low-pass filter includes a first resistor coupled between the third user contact and the third electronics contact and a fourth capacitor coupled to ground between the first resistor and the third electronics contact; and the second low-pass filter includes a second resistor coupled between the fourth user contact and the fourth electronics contact and a fifth capacitor coupled to ground between the second resistor and the fourth electronics contact, the system further comprising:

a third resistor coupled between the first capacitor and the first electronics contact;

a fourth resistor coupled between the second capacitor and the second electronics contact;

a sixth capacitor coupled between the third user contact and the first low-pass filter;

a fifth resistor coupled to a supply voltage and between the sixth capacitor and the first low-pass filter;

a sixth resistor coupled to ground and between the sixth capacitor and first low-pass filter;

a seventh capacitor coupled between the fourth user contact and the second low-pass filter;

a seventh resistor coupled to the supply voltage and between the seventh capacitor and second low-pass filter; and an eighth resistor coupled to ground and between the seventh capacitor and second low-pass filter.

* * * * *